United States Patent [19]
Johnson

[11] Patent Number: 5,206,231
[45] Date of Patent: Apr. 27, 1993

[54] 2,5-BENZODIAZOCINE ANTIARRHYTHMIC AGENTS

[75] Inventor: Robert E. Johnson, East Greenbush, N.Y.

[73] Assignee: Sterling Drug Inc., Rensselaer, N.Y.

[21] Appl. No.: 757,167

[22] Filed: Sep. 10, 1991

[51] Int. Cl.$^5$ .................. A61K 31/44; A61K 31/395; C07D 245/06
[52] U.S. Cl. .................... 514/183; 514/340; 514/352; 514/444; 514/471; 540/473; 540/460
[58] Field of Search ............. 540/473, 460; 514/352, 514/444, 471, 183, 340

[56] References Cited

U.S. PATENT DOCUMENTS

| | | | |
|---|---|---|---|
| 3,496,164 | 2/1970 | Kim et al. | 540/473 |
| 3,663,532 | 5/1972 | Sulkowski | 540/473 |

FOREIGN PATENT DOCUMENTS

| | | | |
|---|---|---|---|
| 59-10572 | 1/1984 | Japan | 540/473 |
| 59-10573 | 1/1984 | Japan | 540/473 |

OTHER PUBLICATIONS

Sulkowski, T. S. et al. "2,5-Benzodiazocines and Intermediates" *J. Org. Chem.* 32:2180–2184 (1967).

Primary Examiner—Robert T. Bond
Assistant Examiner—E. C. Ward
Attorney, Agent, or Firm—Paul E. Dupont

[57] ABSTRACT

Novel 2,5-benzodiazocines of formulas II and IV, pharmaceutical compositions containing them, processes for preparing them and methods of treating cardiac arrhythmias in mammals utilizing them.

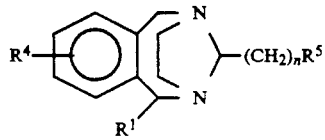

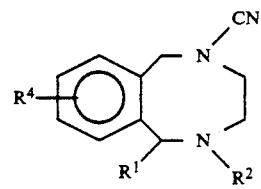

8 Claims, No Drawings

2,5-BENZODIAZOCINE ANTIARRHYTHMIC AGENTS

BACKGROUND OF THE INVENTION

1. Field of the Invention

The present invention relates to novel 2,5-benzodiazocines, to pharmaceutical compositions containing them, to processes for preparing them and to methods of treating cardiac arrhythmia in mammals utilizing them.

2. Information Disclosure Statement

Kim et al. U.S. Pat. No. 3,496,164 discloses a series of 1-aryl-1,2,3,4,5,6-hexahydro-2,5-benzodiazocines having "pharmacological properties" (column 1, line 51).

Sulkowski U.S. Pat. No. 3,663,532 discloses further representatives of the 1-aryl-1,2,3,4,5,6-hexahydro-2,5-benzodiazocines having appetite-suppressant and mood-elevating properties. This disclosure is substantially repeated in Sulkowski et al. [*J. Org. Chem.* 32, 2180–2184 (1967)].

Japanese published applications 59/10572 and 59/10573 (*Chem. Abstr.* 101:23522q and 23523r) disclose 2-alkyl-, 5-alkyl-, or 2,5-dialkyl-1-aryl-1,2,3,4,5,6-hexahydrobenzodzocines as analgesic agents. Also disclosed are the corresponding 2-acyl-, 5-acryl- or 2,5-diacyl compounds as intermediates.

SUMMARY OF THE INVENTION

In a produce aspect, the invention relates to 1-aryl-2,5-benzodiazocines of formula I

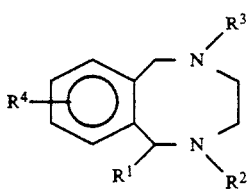

wherein
$R^1$ is phenyl, naphthyl, thienyl, furanyl, pyridinyl, benzyl or phenyl having one or two substitutents chosen from the group consisting of lower-alkyl, lower-alkoxy and halogen;
$R^2$ is a hydrogen or lower-alkyl,
$R^3$ is cyano or
$R^2$ and $R^3$ together are

$R^4$ is one or two substituents chosen independently from the group consisting of lower-alkyl, lower-alkoxy and halogen;
$R^5$ is hydrogen, phenyl, or phenyl having one or two substituents chosen from the group consisting of lower-alkyl, lower-alkoxy and halogen; and n is zero or an integer from one to six.

Preferred compounds are those wherein $R^1$ is phenyl and $R^4$ is hydrogen. When $R^2$ and $R^3$ together are

preferred compounds are those wherein n is zero to two.

In a composition aspect, the invention relates to compositions for the treatment of cardiac arrhythmia which comprise compounds of formula I together with pharmaceutical carriers.

In a method aspect, the invention relates to a method for the treatment of cardiac arrhythmia which comprises administering an antiarrhythmically effective amount of a compound of formula I.

In a process aspect, the invention relates to a process for preparing compounds of formula II

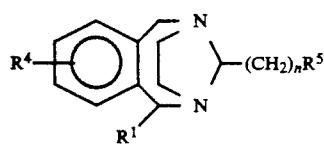

which comprises reacting a benzodiazocine of formula III

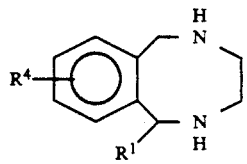

with an aldehyde of formula $R^5$—$(CH_2)_n$—CHO.

In a further process aspect, the invention relates to a process for preparing compounds of formula IV

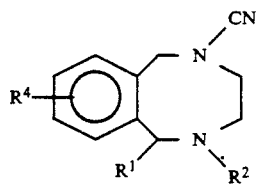

which comprises reacting a benzodiazocine of formula V

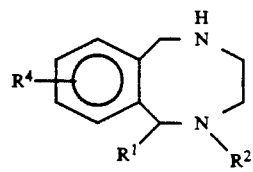

with cyanogen bromide or cyanogen chloride.

Lower-alkyl as used herein describes linear, branched, or cyclic saturated carbon chains of six or fewer carbon atoms; lower-alkoxy as used herein describes linear or branched alkoxy substituents containing six or fewer carbon atoms; halogen describes bromine, chlorine or fluorine.

In the text that follows, the substituents R are defined when initially presented and maintain that definition whenever they occur subsequently.

DETAILED DESCRIPTION INCLUSIVE OF PREFERRED EMBODIMENTS

The compounds of the invention may be synthesized from 1-aryl-1,2,3,4,5,6-hexahydro-2,5-benzodiazocines as shown below:

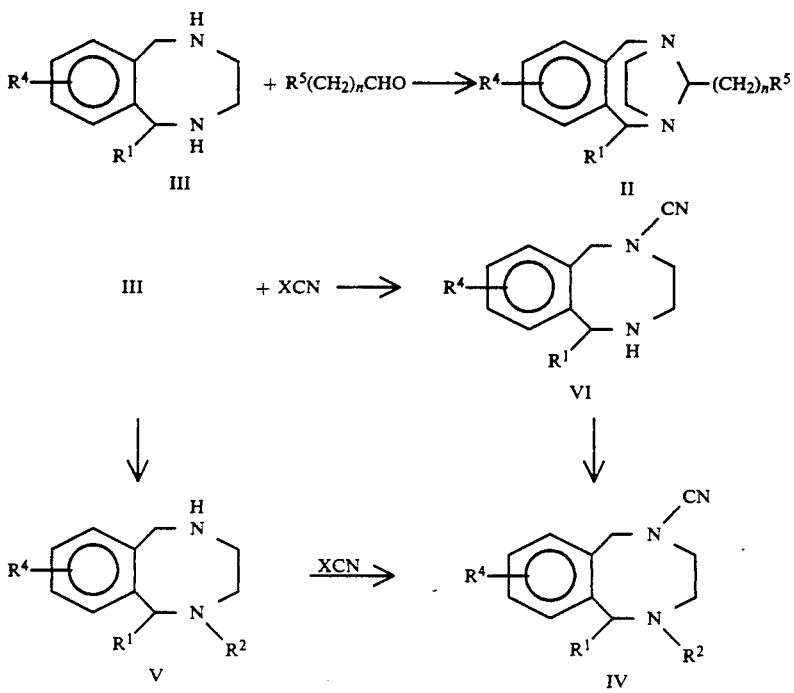

To provide diazocines of the subgenus II, a diazocine of formula III is reacted with a slight excess of the appropriate aldehyde in a solvent, preferably ethanol, at 20° to the boiling point of the solvent. To provide diazocines of the subgenus IV, a diazocine of formula III is reacted with one equivalent of cyanogen bromide or chloride, preferably bromide, in a solvent, preferably methanol, at 0° to 50°. The produce is predominantly the mononitrile VI. If it is desired that $R^2$ be lower-alkyl, the nitrile VI may be alkylated with a lower-alkyl bromide or iodide either in the presence of a base such as potassium carbonate or by preforming the anion of VI with a base such as sodium hydride and alkylating the anion. Alternatively, the diazocine III may be reacted at $N^5$ with a source of a protecting acyl group, such as t-butoxycarbonyl, then at $N^2$ with the appropriate alkylating agent, followed by deprotection of $N^5$ to provide the $N^2$-alkylated diazocine V, which may then be reacted as above to produce 2-lower-alkyl diazocine-carbonitriles of formula IV.

The 1-aryl-1,2,3,4,5,6-hexahydro-2,5-benzodiazocines, which are the starting materials for the compounds of the invention, are available by the methods described in U.S. Pat. No. 3,663,532 from the condensation of 2-ketobenzoic acids with ethylenediamine followed by hydride reduction. Syntheses of 2-ketobenzoic acids not described in U.S. Pat. No. 3,663,532, that can be used as starting materials are given below.

It will be noted that compounds of the invention are asymmetric at C-1 of the benzodiazocine. In some cases there may be an advantage to using one or the other enantiomer for the treatment of arrhythmia. Single enantiomers may be synthesized from chiral starting materials or the racemates may be resolved by methods well known in the art, such as chromatography on chiral media or recrystallization of diastereomeric salts.

The compounds of the invention are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. In practicing the present invention, it is convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, nuclear magnetic resonance, and mass spectroscopy. The course of the reactions and the identity and homogeneity of the products were assessed by thin layer chromatography (TLC) and high-pressure liquid chromatography (HPLC).

In the following procedures, melting points are given in degrees C. and are uncorrected.

In the examples which follow, Me is methyl, Et is ethyl, Ph is phenyl, Bzl is benzyl, Bu is butyl, OAc is acetyl, THF is tetrahydrofuran, and DMF is dimethylformamide.

Preparation 1

A solution of 30 g of potassium hydroxide and 31.3 g (140 mmol) of benzylidenephthalide in 100 mL of water was heated to homogeneity and poured into a solution of 40 mL of $H_2SO_4$ in 250 mL of water. After cooling, the resulting solid was collected and dissolved in aqueous sodium bicarbonate. 2N HCl was added until the first signs of precipitation, the aqueous solution was washed four times with chloroform and then acidified with excess 2N HCl. A white precipitate of 20.3 g of 2-(1-oxo-2-phenylethyl)benzoic acid was filtered off and dried, mp 74–75, after recrystallization from ethanol water.

Following the procedure of U.S. Pat. No. 3,663,532, it is contemplated that 2-(1-oxo-2-phenylethyl)benzoic acid may be converted to 1-benzyl-1,2,3,4,5,6-hexahydro-2,5-benzodiazocine (III: $R^1$=Bzl, $R^4$=H).

Preparation 2

One hundred grams (0.58 mol) of 2-bromotoluene was added to 14.2 g (0.58 mol) of magnesium turnings in 425 mL of warm ether. Reaction was initiated with iodine and the bromotoluene was added at a rate to maintain gentle reflux. After 1 hour of further reflux, 30.4 g (0.29 mol of 4-cyanopyridine in 375 mL of ether was added dropwise over the course of 2 hours. The reaction was cooled, 430 mL of 6 HCl was added with stirring and the mixture was allowed to stand overnight. The layers were separated, the aqueous layer made basic (pH 8) with 35% aqueous NaOH, and the product extracted into ether. The ether was dried and stripped to provide 45.9 g of 2-methylphenyl-4-pyridinylketone as an oil.

The ketone (0.23 mol) was suspended in 25 L of water with 28 g (0.23 mol) of $MgSO_4$, refluxed and 159.9 g (1.01 mol) of potassium permanganate was added in portions at reflux. The reaction was refluxed for 4 hours, let stand overnight, filtered through celite, stripped to 500 mL, and 500 mL of ethanol was added. The solution was filtered and glacial acetic acid was added until a white precipitate formed. It was filtered off and dried to provide 18.9 g (36%) of 2-(4-pyridinylcarbonyl)benzoic acid.

Following the procedure of U.S. Pat. No. 3,663,532, it is contemplated that 2-(4-pyridinylcarbonyl)benzoic acid may be converted to 1-(4-pyridinyl)-1,2,3,4,5,6-tetrahydro-2,5-benzodiazocine (III: $R^1$=pyridinyl, $R^4$=H).

EXAMPLE 1

3,4-Dihydro-11-ethyl-1-phenyl-2,5-methano-1H,6H-2,5-benzodiazocine (II: $R^1$=Ph, $R^4$=$R^5$=H, n=2)

A mixture of 3 g (12.6 mmol) of 1,2,3,4,5,6-hexahydro-1-phenyl-2,5-benzodiazocine and 0.84 (14.5 mmol) of propionaldehyde in 40 mL of ethanol was refluxed for 30 min, cooled, stripped, dissolved in ethyl acetate and a small amount of impurity crystallized by the addition of hexane. After filtering, the mother liquor was stripped and crystallized from pentane by chilling and collecting at 0°. There was obtained a first crop of 1.53 g of 3-4-dihydro-11-ethyl-1-phenyl-2,5-methano-1H,6H-2,5-methano-1H, 6H-2,5-benzodiazocine, mp 66°–67°.

EXAMPLE 2

4,5-Dihydro-1,11-diphenyl-2,5,-methano-1H,6H-2,5-benzodiazocine (II: $R^1$=$R^5$=Ph, $R^4$=H, n=0)

A mixture of 2 g (8.4 mmol) of 1,2,3,4,5,6-hexahydro-1-phenyl-2,5-benzodiazocine and 1.0 g (9.2 mmol) of benzaldehyde in 40 mL of ethanol was refluxed for 30 min, cooled on ice and the product filtered off. There was obtained 2.33 g of 3,4-dihydro-1,11-diphenyl-2,5-methano-1H,6H-2,5-benzodiazocine, mp 175°–176°.

EXAMPLE 3–7

By a process analogous to that of examples 1 and 2, it is contemplated that the following methano benzodiazocines may be obtained:

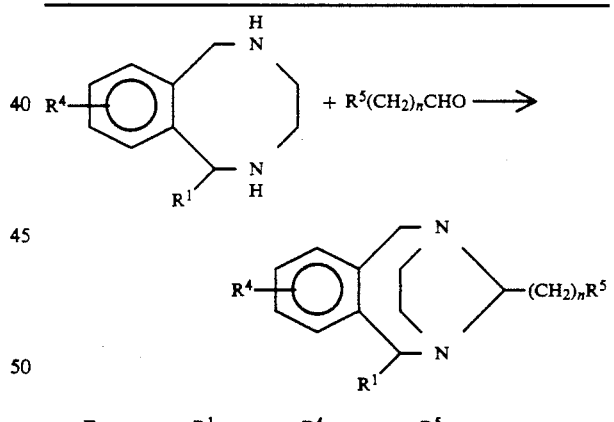

| Ex | $R^1$ | $R^4$ | $R^5$ | n |
|---|---|---|---|---|
| 3 | 2-thienyl | H | Ph | 2 |
| 4 | 4-pyridinyl | H | 4-MeO—Ph | 2 |
| 5 | 1-napthyl | MeO | 2,3-$Cl_2$—Ph | 0 |
| 6 | benzyl | H | Ph | 1 |
| 7 | Ph | Me | H | 6 |

EXAMPLE 8

6-Phenyl-3,4,5,6-tetrahydro-2,5-benzodiazocine-2(1H)-carbonitrile (IV: $R^1$=Ph, $R^2$=$R^4$=H)

A solution of 6.87 g (63 mmol) of cyanogen bromide in 15 mL of methanol was added to a solution of 15 g (63 mmol) of 1,2,3,4,5,6-hexahydro-1-phenyl-2,5-benzodiazocine in 110 mL of methanol at 0°. The reaction was allowed to come to room temperature and stirred 3 hours. The reaction was stripped and the residue partitioned between ethyl acetate and water made slightly acidic with 6N HCl. The aqueous layer was made basic, extracted into ethyl acetate, dried, stripped and chromatographed on ten times its weight of silica gel, eluting with 1:9 ethyl acetate/dichloromethane. There was obtained 5.93 g of 6-phenyl-3,4,5,6-tetrahydro-2,5-benzodiazocine-2(1H)-carbonitrile, mp 134°–135° from dichloromethane/ether/hexane.

The compounds of this invention have antiarrhythmic activity as shown by the results of standard pharmacological tests carried out on representative examples as described below.

Antiarrhythmic activity was demonstrated by a procedure, which is a modification of standard programmed electrophysiological techniques utilized in large animals and in clinical studies in humans. Male Duncan-Hartley guinea pigs (600–800 grams) were anesthetized with sodium pentobarbital (30 mg/kg, i.p.) and artificially ventilated with a Harvard small-animal respirator. A left thoracotomy was performed and a fluid-filled catheter and transducer (Millar Micro-tip, Model 4F, Millar Inst. Inc., Houston, Tex.) were inserted through the anterior wall of the left ventricle to monitor left ventricular pressure (LVP). The first derivative of the LVP (dP/dt) was obtained from a Grass differentiator (Model 7P20B) and used as an index of contractile function. A lead II EKG along with LVP and dP/dt were continuously recorded on a Grass polygraph (Model 7B). Rate pressure product (RPP), an index of cardiac work, was calculated using peak systolic LVP and heart rate (HR).

Effective refractory periods (ERP) were evaluated during left ventricular pacing. Grass subcutaneous electrodes were implanted as bipolar ventricular electrodes to deliver stimuli from a Bloom DTU-2 stimulator (Bloom Electronics, Inc., Reading, Pa.) and stimulus isolation unit. Hearts were stimulated at the slowest frequency allowing consistent pacing (S1, 240–300 bpm) using 2 ms pulses at twice diastolic threshold. Threshold was determined by increasing the stimulation voltage until a 1:1 capture of the ventricular response with the stimulus was observed. A train of 8 normal pulses was delivered followed by a premature (S2) pulse. The interval between the last S1 and the premature S2 pulse was reduced in 10-ms increments until a ventricular response was not initiated. The longest S1-S2 interval that failed to produce a ventricular response was defined as the ERP. Pacing stimuli and the EKG were displayed at a sampling frequency of 92 Hz on an Apple IIe microcomputer using a two-channel 8-bit A/D converter (R. C. Electronics, Compu-Scope APL-D2, Santa Barbara, Calif.).

Baseline hemodynamic function was evaluated followed by ventricular pacing to determine ERP. Pacing was discontinued prior to drug administration and resumed at set intervals during the protocol to evaluate ERP. Test compounds were administered (1 mL/kg) via the left ventricular catheter over a 15-second interval for doses less than 10 mg/kg. Higher doses (>10 mg/kg) were slowly infused over a 1-minute interval. Doses were cumulatively increased every 15 minutes until a maximally tolerated dose which reduced dP/dt by 50% was noted. Ten minutes after each dose, hemodynamics and ERP were reevaluated.

Data were analyzed using an analysis of variance for repeated measures of raw data and are expressed as means. An effective dose to increase ERP by a minimum of 20 msecs ($ED_{20}$), which was consistently a statistically significant increase, was derived for each animal from a linear regression of the data and expressed as a mean for the treated population. Biological significance was established at a probability of error less than 0.05. The results are presented in Table A.

TABLE A

| Example | $ED_{20}$ mg/kg |
| --- | --- |
| 1 | 4.8 |
| 2 | 4.9 |
| 8 | 0.01 |

The pharmaceutical compositions of the present invention include one or more of the compounds of this invention formulated into compositions together with one or more nontoxic physiologically acceptable carriers, adjuvants or vehicles which are collectively referred to herein as carriers, for parenteral injection, for oral administration in solid or liquid form, for rectal or topical administration, and the like.

The compositions can be administered to humans and animals either orally, rectally, or parenterally (intravenously, intramuscularly or subcutaneously).

Compositions suitable for parenteral injection may comprise physiologically acceptable sterile aqueous or nonaqueous solutions, dispersions, suspensions or emulsions and sterile powders for reconstitution into sterile injectable solutions of dispersions. Examples of suitable aqueous and nonaqueous carriers, diluents, solvents or vehicles include water, ethanol, polyols (propylene glycol, polyethylenegylcol, glycerol and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents for example sugars, sodium chloride and the like. Prolonged absorption of the injectable pharmaceutical form can be brought about by the use of agents delaying absorption; for example, aluminum monostearate and gelatin.

Solid dosage forms for oral administration include capsules, tablets, pills, powders and granules. In such solid dosage forms, the active bacteria is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboyxmethylcellulose, alginates, gelatin, polyvinylpyrrolidione, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaoline and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

I claim:

1. A compound of formula

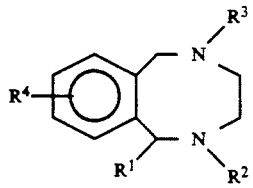

or acid-addition salt thereof wherein $R^1$ is phenyl, naphthyl, thienyl, pyridinyl, furanyl, benzyl, or phenyl having one or two substitutents chosen independently from the group consisting of lower-alkyl, lower-alkoxy and halogen;

$R^2$ is hydrogen or lower-alkyl, $R^3$ is cyano; and $R^4$ is one or two substituents chosen independently from the group consisting of hydrogen lower-alkyl, lower-alkoxy and halogen.

2. 6-phenyl-3,4,5,6-tetrahydro-2,5-benzodiazocine-2(1H)-carbonitrile according to claim 1.

3. A composition for the treatment of cardiac arrhythmia in a patient in need of such treatment which comprises a pharmaceutical carrier and an antiarrhythmically effective amount of a compound according to claim 1.

4. A composition for the treatment of cardiac arrhythmia in a patient in need of such treatment which comprises a pharmaceutical carrier and an antiarrhythmically effective amount of a compound according to claim 2.

5. A method for the treatment of cardiac arrhythmia in a patient in need of such treatment which comprises the administration of an antiarrhythmically effective amount of a compound according to claim 1.

6. A method for the treatment of cardiac arrhythmia in a patient in need of such treatment which comprises the administration of an antiarrhythmically effective amount of a compound according to claim 2.

7. A method for the treatment of cardiac arrhythmia in a patient in need of such treatment which comprises the administration of a composition according to claim 3.

8. A method for the treatment of cardiac arrhythmia in a patient in need of such treatment which comprises the administration of a composition according to claim 4.

* * * * *